United States Patent [19]
Ono et al.

[11] Patent Number: 6,083,171
[45] Date of Patent: *Jul. 4, 2000

[54] BLOOD PRESSURE MONITORING APPARATUS

[75] Inventors: Kohei Ono; Hiromitsu Kasuya; Yoshihiro Sugo; Takeshi Sohma; Hidehiro Hosaka, all of Tokyo, Japan

[73] Assignee: Nihon Kohden Corporation, Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/742,750

[22] Filed: Nov. 1, 1996

[30] Foreign Application Priority Data

Nov. 2, 1995 [JP] Japan .................... 7-285669

[51] Int. Cl.$^7$ .................................................. A61B 05/00
[52] U.S. Cl. .......................... 600/494; 600/495; 600/500
[58] Field of Search .................................. 600/485, 490, 600/493–496, 500

[56] References Cited

U.S. PATENT DOCUMENTS

| | | | |
|---|---|---|---|
| 4,566,463 | 1/1986 | Taniguchi et al. | 128/682 |
| 4,807,638 | 2/1989 | Sramek | 400/485 |
| 4,907,596 | 3/1990 | Schmid et al. | 600/500 |
| 5,237,997 | 8/1993 | Greubel et al. | 600/500 |
| 5,279,303 | 1/1994 | Kawamura et al. | 128/683 |
| 5,564,427 | 10/1996 | Aso et al. | 128/681 |
| 5,603,329 | 2/1997 | Hosaka et al. | 600/500 |
| 5,649,543 | 7/1997 | Hosaka et al. | 600/500 |

FOREIGN PATENT DOCUMENTS

| | | |
|---|---|---|
| 26 05 528 A1 | 2/1976 | Germany . |
| 62-155829 | 7/1987 | Japan . |
| 2-45033 | 2/1990 | Japan . |
| 2-82309 | 6/1990 | Japan . |
| 4-200439 | 7/1992 | Japan . |
| 4-367648 | 12/1992 | Japan . |

*Primary Examiner*—Robert L. Nasser
*Attorney, Agent, or Firm*—Sughrue, Mion, Zinn, Macpeak & Seas, PLLC

[57] ABSTRACT

A pulse wave propagation time is counted constantly. Not only it is judged whether or not a pulse wave propagation time change $\Delta T$ exceeds a pulse wave propagation time change threshold $\Delta Ts$, but also it is judged whether or not cardiovascular dynamic changes $\Delta HR$, $r_1$, $r_2$ exceed thresholds thereof $\Delta HRs$, $r_1s$, $r_2s$, whereby a sudden turn for the worse in the blood pressure fluctuation of a subject is monitored. If any one of the changes exceeds the threshold thereof, a blood pressure measurement using a cuff 2 is made on the subject.

30 Claims, 3 Drawing Sheets

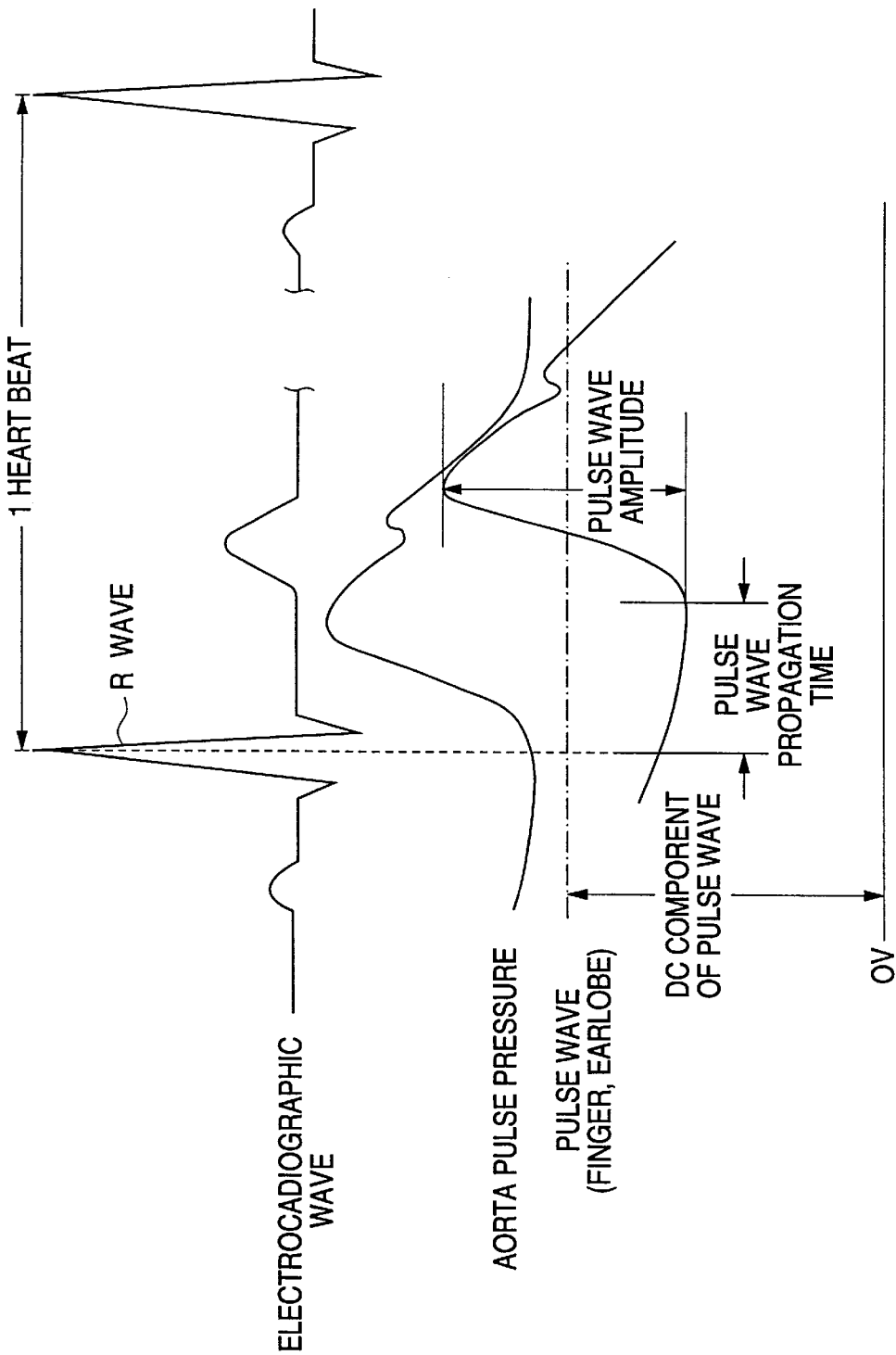

BLOOD PRESSURE MONITORING APPARATUS

BACKGROUND OF THE INVENTION

1. Field of the Invention

The invention relates to blood pressure monitoring apparatuses to be applied to such fields as requiring continuous blood pressure monitoring for subjects to be treated in operating rooms, intensive care units, emergency treatment rooms, artificial dialysis treatment rooms, and the like. More particularly, the invention is directed to a blood pressure monitoring apparatus that monitors blood pressure by means of pulse wave propagation time.

2. Related Art

Known as a blood pressure monitoring apparatus that monitors blood pressure by continuously measuring the blood pressure of a subject are a noninvasive blood pressure measurement type based on an oscillometric method by wrapping a cuff around the brachium of a subject and an invasive blood pressure measurement type that involves insertion of an instrument into the aorta of the subject.

By the way, a conventional blood pressure monitoring apparatus has addressed the following problems.

(1) In a blood pressure monitoring apparatus that measures blood pressure in a noninvasive manner using a cuff, the problem arises when blood pressure is measured regularly at a long time interval. That is, a sudden turn for the worse such as a shock in blood pressure has, in some cases, been missed when the blood pressure is measured at a time interval exceeding 5 minutes, for example. It may be noted that by shortening the measuring cycle to, e.g., 1 minute, the likelihood of missing sudden changes in blood pressure can be reduced. However, when the measuring cycle is shortened, burden is given to the blood vessel of a body part around which the cuff is wrapped.

(2) Further, when blood pressure is measured regularly, the subject is burdened with the part of his or her body being pressured with the cuff more frequently than necessary.

(3) In a blood pressure monitoring apparatus of the invasive measurement type, the subject may, in some cases, be spiritually burdened by stress. Further, such blood pressure monitoring apparatus entails more cumbersome operation than a blood pressure monitoring apparatus of the noninvasive blood pressure measurement type, which in turn burdens the medical staff as well.

Therefore, the object of the invention is to provide a blood pressure monitoring apparatus that can monitor blood pressure continuously, safely, and highly accurately without giving burden to a subject.

According to an aspect of the present invention, there is provided a blood pressure monitoring apparatus including a blood pressure measuring means for measuring blood pressure using a cuff; a storage means for storing a pulse wave propagation time change threshold and a cardiovascular dynamic change threshold, both thresholds being inputted from an external means; a time interval detection reference point detecting means for detecting a time interval detection reference point on a pulse wave at an aorta of a body; a pulse wave detecting means for detecting a pulse wave at a peripheral blood vessel appearing with a time delay with respect to the pulse wave at the aorta; a pulse wave propagation time counting means for counting a pulse wave propagation time based on detected outputs from the time interval detection reference point detecting means and the pulse wave detecting means; a pulse wave propagation time change calculating means for calculating a pulse wave propagation time change from the two pulse wave propagation times counted by the pulse wave propagation time counting means; a cardiovascular dynamic change calculating means for calculating a cardiovascular dynamic change from the time interval detection reference point or the pulse wave at the peripheral blood pressure; a first judging means for judging whether or not the pulse wave propagation time change calculated by the pulse wave propagation time change calculating means exceeds the pulse wave propagation time change threshold stored in the storage means; a second judging means for judging whether or not the cardiovascular dynamic change calculated by the cardiovascular dynamic change calculating means exceeds the cardiovascular dynamic change threshold stored in the storage means; and a control means for controlling the blood pressure measuring means and for measuring blood pressure of a subject using the cuff if it is judged that the pulse wave propagation time change exceeds the pulse wave propagation time change threshold or if it is judged that the cardiovascular dynamic change exceeds the cardiovascular dynamic change threshold.

The present invention is provided as using a value equivalent to a heart rate change as a cardiovascular dynamic change threshold, causing the cardiovascular dynamic change calculating means to calculate a heart rate change based on the time interval detection reference point, and by causing the second judging means to judge whether or not the heart rate change exceeds the cardiovascular dynamic change threshold equivalent to the heart rate change.

The present invention is provided as using a value equivalent a rate of change of an amplitude of a pulse wave of a peripheral blood vessel as a cardiovascular dynamic change threshold, and causing the cardiovascular dynamic change calculating means to calculate the rate of change of the amplitude of the pulse wave of the peripheral blood vessel based on the pulse wave at the peripheral blood vessel, and causing the second judging means to judge whether or not the rate of change of the amplitude of the pulse wave exceeds the cardiovascular dynamic change threshold equivalent to the rate of change of the amplitude of the pulse wave of the peripheral blood vessel.

The present invention is provided as using a value equivalent to a rate of change of a dc component of a pulse wave of a peripheral blood vessel as a cardiovascular dynamic change threshold, causing the cardiovascular dynamic change calculating means to calculate the rate of change of the dc component of the pulse wave based on the pulse wave at the peripheral blood vessel, and causing the second judging means to judge whether or not the rate of change of the dc component of the pulse wave exceeds the cardiovascular dynamic change threshold equivalent to the rate of change of the dc component of the pulse wave of the peripheral blood vessel.

The present invention is provided as using a heart rate change, a rate of change of an amplitude of a pulse wave of a peripheral blood vessel, and a rate of change of a dc component of a pulse wave of a peripheral blood vessel as cardiovascular dynamic change thresholds; causing the cardiovascular dynamic change calculating means to calculate not only the heart rate change based on the time interval detection reference point, but also the rate of change of the amplitude of the pulse wave and the rate of change of the dc component of the pulse wave based on the pulse wave at the peripheral blood vessel; causing the second judging means to judge whether or not the heart rate change exceeds the cardiovascular dynamic change threshold equivalent to the heart rate change, whether or not the rate of change of the amplitude of the pulse wave exceeds the cardiovascular dynamic change threshold equivalent to the rate of change of the amplitude of the pulse wave of the peripheral blood vessel, and whether or not the rate of change of the dc component of the pulse wave exceeds the cardiovascular dynamic change threshold equivalent to the rate of change of the dc component of the peripheral blood vessel; and causing the control means to control the blood pressure measuring means and to measure blood pressure of a subject using the cuff if it is judged that the heart rate change exceeds the cardiovascular dynamic change threshold equivalent to the heart rate change, if it is judged that the rate of change of the amplitude of the pulse wave exceeds the cardiovascular dynamic change threshold equivalent to the rate of change of the amplitude of the pulse wave of the peripheral blood vessel, or if it is judged that the rate of change of the dc component of the pulse wave exceeds the cardiovascular dynamic change threshold equivalent to the rate of change of the dc component of the pulse wave of the peripheral blood vessel.

As described in the foregoing, the blood pressure monitoring apparatuses of the present invention are provided as not only judging whether or not the pulse wave propagation time change exceeds the preset pulse wave propagation time change threshold, but also judging whether or not the cardiovascular dynamic change, i.e., the heart rate change, the rate of change of the amplitude of the pulse wave at the peripheral blood vessel, or the rate of change of the dc component of the pulse wave at the peripheral blood vessel, exceed the preset cardiovascular dynamic change thresholds thereof and starting a blood pressure measurement for the subject if any one of the changes is judged to exceed the threshold thereof. There fore, the burden given to the subject in the past can be reduced. In addition, the blood pressure monitoring apparatuses of the present invention are also characterized as allowing a feeble blood pressure fluctuation that cannot be detected by the pulse wave propagation time change to be detected by the cardiovascular dynamic change. Therefore, a sudden turn for the worse in the blood pressure fluctuation of the subject can be monitored more reliably.

BRIEF DESCRIPTION OF THE DRAWINGS

FIG. 3 is a waveform diagram illustrative of a pulse wave propagation time.

DETAILED DESCRIPTION OF THE PREFERRED EMBODIMENTS

The basic concept of the invention will hereunder be described.

In a blood pressure monitoring apparatus of the noninvasive measurement type utilizes pulse wave propagation velocity (pulse wave propagation time at a predetermined distance).

The principle of a blood pressure measuring method based on pulse wave propagation velocity is as follows.

As shown in FIG. 3, the specific point of a pulse wave on the peripheral blood vessel side appears with a delay with respect to the specific point of an aortic pulse wave. This delay time is the pulse wave propagation time.

A pulse wave propagation velocity corresponding to a pulse wave propagation time at a predetermined distance appears as a function of the volume elasticity of a blood vessel. The volume elasticity of a blood vessel increases with increasing blood pressure, and the blood vessel wall becomes hard, which in turn increases propagation velocity.

Therefore, blood pressure fluctuations can be calculated from pulse wave propagation velocity. By consecutively measuring the pulse wave propagation time, the blood pressure fluctuations of a subject can be monitored. In this case, when a pulse wave propagation time change $\Delta T$ exceeds a preset pulse wave propagation time change threshold $\Delta Ts$, or when a heart rate change $\Delta HR$ exceeds a cardiovascular dynamic change threshold $\Delta HRs$ equivalent to a preset heart rate change, or when a rate of change of the amplitude of a pulse wave of a peripheral blood vessel $r_1$ exceeds a cardiovascular dynamic change threshold $r_1s$ equivalent to a preset rate of change of the amplitude of a pulse wave of a peripheral blood vessel, or when a rate of change of the dc component of a pulse wave of a peripheral blood vessel $r_2$ exceeds a cardiovascular dynamic change threshold $r_2s$ equivalent to a preset rate of change of the dc component of a pulse wave of a peripheral blood vessel, then it is judged that a sudden turn for the worse in the blood pressure fluctuation has occurred on a subject, and a non-invasive blood pressure measurement using the cuff is made at such timing.

In this case, the heart rate change $\Delta HR$, the rate of change of the amplitude of the pulse wave of the peripheral blood vessel $r_1$, and the rate of change of the dc component of the pulse wave of the peripheral blood vessel $r_2$ are cardiovascular dynamic changes, and these changes are more critical than the pulse wave propagation time change $\Delta T$. Therefore, these changes can detect even a feeble change in blood pressure which cannot be detected by the pulse wave propagation time. As a result, a sudden turn for the worse in blood pressure fluctuation can be monitored with extremely high accuracy.

A blood pressure monitoring apparatus, which is an embodiment of the invention, will now be described with reference to the drawings.

A. Configuration of the Blood Pressure Monitoring Apparatus

Figure 1:
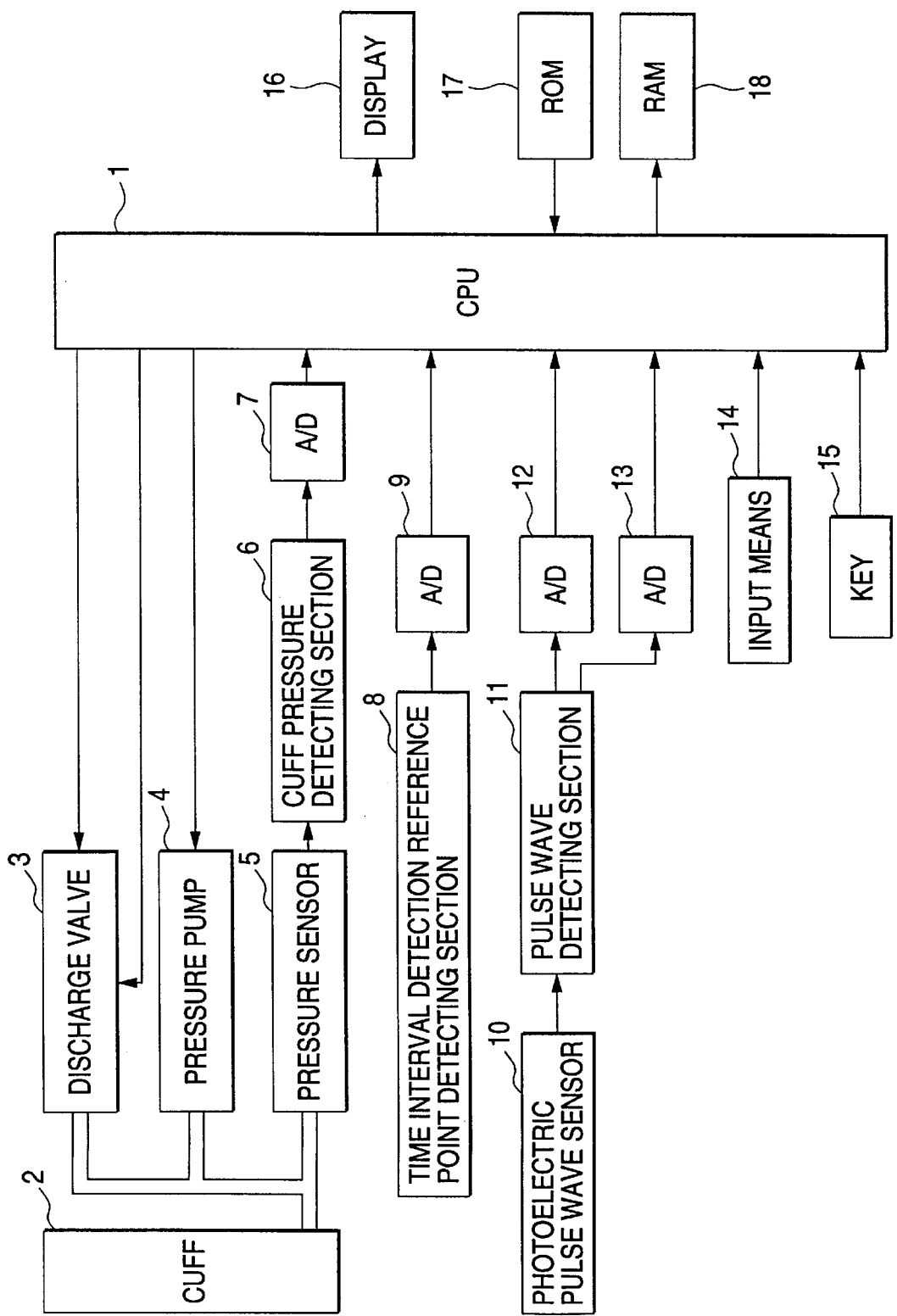
FIG. 1 is a block diagram showing a configuration of a blood pressure monitoring apparatus, which is an embodiment of the invention.

FIG. 1 is a block diagram showing an exemplary configuration of the blood pressure monitoring apparatus of the invention. In FIG. 1, a cuff 2 is designed to be attached to a brachium or finger of a subject and the inside thereof is opened or closed with respect to the atmosphere by a discharge valve 3. Air is supplied to the cuff 2 by a pressure pump 4. A pressure sensor 5 is arranged on the cuff main body, and the output of the sensor is detected by a cuff pressure detecting section 6. The output of the cuff pressure detecting section 6 is converted into a digital signal by an A/D converter 7 and is received by a CPU (central processing unit) 1.

A time interval detection reference point detecting section 8 is provided to detect a timing at which the aortic blood pressure reaches a bottom value thereof substantially simultaneously with generation of an ECG R wave. The output of this detecting section 8 is received by the CPU 1 while converted into a digital signal by an A/D converter 9. The time interval detection reference point detecting section 8 can be constructed of electrodes that are attached to the chest of a subject and an ECG R wave detecting section to which the electrodes are connected. It may be noted that the time interval detection reference point detecting section 8 can be constructed also of a photoelectric pulse wave sensor or pressure pulse wave sensor for detecting an aortic pulse wave, and a pulse wave detecting section to which such sensor is connected.

A photoelectric pulse wave sensor 10 is attached to, e.g., a finger of a subject to measure pulse waves at peripheral blood vessels. When the output of the photoelectric pulse wave sensor 10 is sent to a pulse wave detecting section 11, the pulse wave at a position of the subject to which the sensor is attached can be detected. The pulse wave detecting section 11 outputs signals by separating the pulse wave into an ac component and a dc component. The ac component of the pulse wave is received by the CPU 1 while converted into a digital signal by an A/D converter 12. Further, the dc component of the pulse wave is received by the CPU 1 while converted into a digital signal by an A/D converter 13.

An input means 14 receives an initial pulse wave propagation time change threshold $\Delta Ts$, and initial cardiovascular dynamic change thresholds $\Delta HRs$, $r_1s$, and $r_2s$. In this case, $\Delta HRs$ is a value equivalent to a change in heart rate; $r_1s$ is a value equivalent to the rate of change in the amplitude of a pulse wave of a peripheral blood vessel; $r_2s$ is a value equivalent to the rate of change in the dc component of a pulse wave of a peripheral blood vessel. A key 15 is pressed when blood pressure is measured manually using the cuff 2.

The CPU 1 executes a processing program based on signals given from the A/D converters 7, 9, 12, 13 and the key 15, outputs necessary control signals to the discharge valve 3, the pressure pump 4, and the like, and supplies the processing result to a display 16. A ROM 17 that is connected to the CPU 1 has the processing program stored therein. Further, in a RAM 18 are various registers and data areas arranged for storing blood pressure measurement data.

The following registers are arranged.

$RT_1$: Register for storing a pulse wave propagation time $T_1$ $RT_2$: Register for storing a pulse wave propagation time $T_2$ $RHR_1$: Register for storing a heart rate $HR_1$ $RHR_2$: Register for storing a heart rate $HR_2$ $RAC_1$: Register for storing an amplitude $AC_1$ of a pulse wave of a peripheral blood vessel $RAC_2$: Register for storing an amplitude $AC_2$ of a pulse wave of a peripheral blood vessel $RDC_1$: Register for storing a dc component $DC_1$ of a pulse wave of a peripheral blood vessel $RDC_2$: Register for storing a dc component $DC_2$ of a pulse wave of a peripheral blood vessel The cuff 2, the discharge valve 3, the pressure pump 4, the pressure sensor 5, the cuff pressure detecting section 6, and the A/D converter 7 constitute a blood pressure measuring means. The RAM 18 corresponds to a storage means. The time interval detection reference point detecting section 8 and the A/D converter 9 constitute a time interval detection reference point detecting means. The photoelectric pulse wave sensor 10, the pulse wave detecting section 11, and the A/D converters 12, 13 constitute a pulse wave detecting means. The CPU 1 corresponds to a pulse wave propagation time counting means, a pulse wave propagation time change calculating means, a cardiovascular dynamic change calculating means, a first judging means, a second judging means, and a control means.

B. Operation of the Blood Pressure Monitoring Apparatus

Then, an operation of the thus constructed blood pressure monitoring apparatus will be described.

Figure 2:
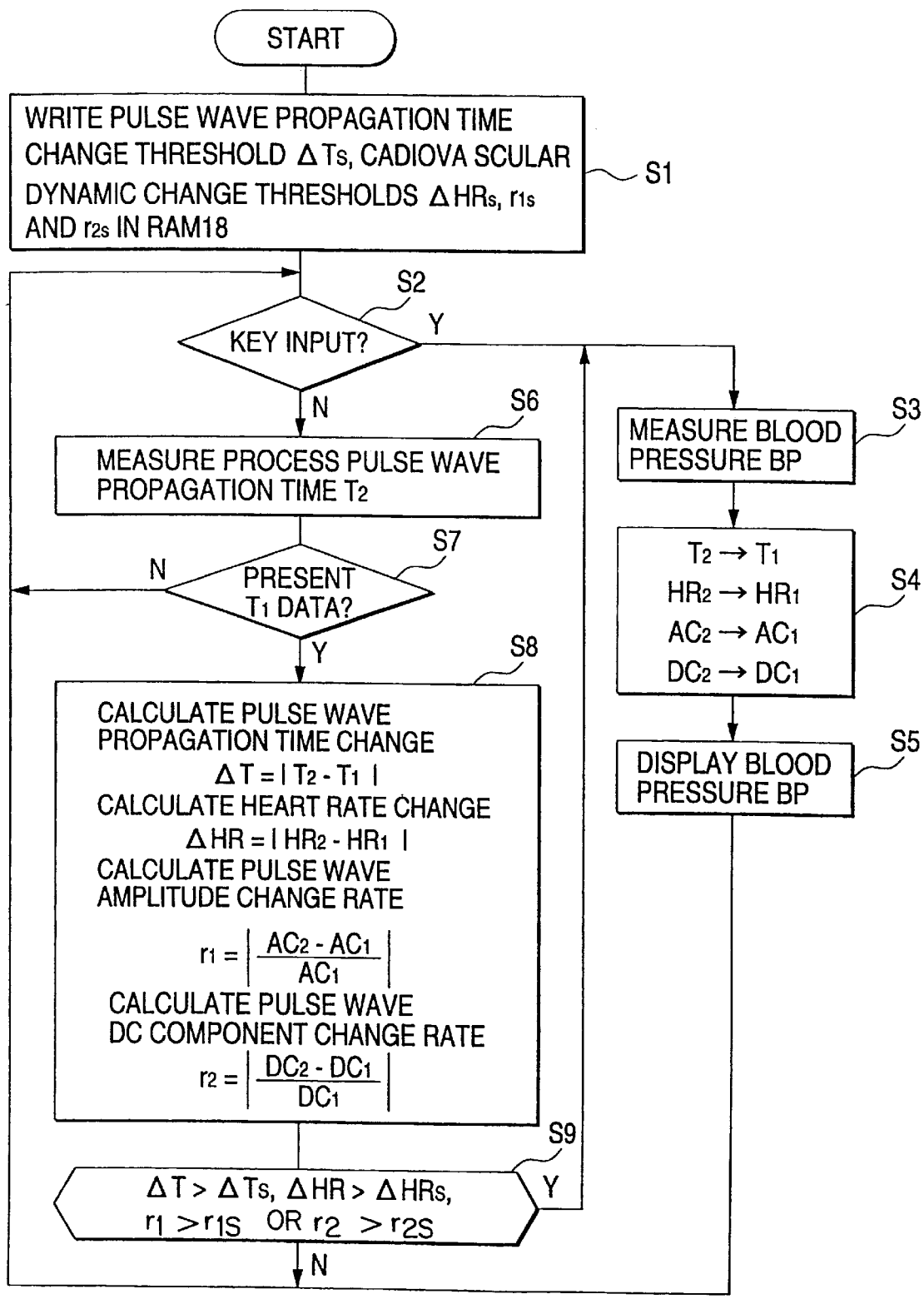
FIG. 2 is a flowchart showing an operation of the blood pressure monitoring apparatus shown in FIG. 1.

FIG. 2 is a flowchart showing an operation of the blood pressure monitoring apparatus.

First, in Step S1, the pulse wave propagation time change threshold $\Delta Ts$, the cardiovascular dynamic change thresholds $\Delta HRs$, $r_1s$, and $r_2s$ are inputted from the input means 14 and written to the RAM 18. It may be noted that these thresholds $\Delta Ts$, $\Delta HRs$, $r_1s$, and $r_2s$ are preset by the weight, height, etc. of a subject.

After the respective thresholds have been written to the RAM 18, it is judged in Step S2 whether or not an input is given through the key 15. If it is judged affirmatively, the discharge valve 3 and the pressure pump 4 are controlled by the CPU 1 in Step S3, and a blood pressure measurement is made on a subject using the cuff 2. Data received from the A/D converter 7 is processed internally by the CPU 1, and a blood pressure value BP measured by an oscillometric method is written to the RAM 18.

After the blood pressure value BP has been written, Step S4 is executed. That is, in Step S4, the pulse wave propagation time $T_2$ stored in the register $RT_2$ is moved to the register $RT_1$; the heart rate $HR_2$ stored in the register $RHR_2$ is moved to the register $RHR_1$; the amplitude $AC_2$ of the pulse wave stored in the register $RAC_2$ is moved to the register $RAC_1$; and the dc component $DC_2$ of the pulse wave stored in the register $RDC_2$ is moved to the register $RDC_1$. In this case, if the pulse wave propagation time $T_2$ is not counted, the operation of moving the data to the registers $RT_1$, $RHR_1$, $RAX_1$, and $RDC_1$ is not actually performed. After the data have been moved from one register to another, the previously measured blood pressure value BP is displayed on the display 16 in Step S5. Then, Step S2 will be executed.

In Step S2, whether or not an input has been made through the key is judged again. If it is judged negatively, the pulse wave propagation time $T_2$ equivalent to a time interval from a timing at which an aortic pulse wave reaches the bottom value thereof substantially simultaneously with generation of an ECG R wave to a timing at which the pulse wave at a peripheral blood vessel reaches the bottom value thereof based on data from the A/D converters 9, 12, and the measured value is stored in the register $RT_2$ of the RAM 18 in Step S6. Further, the heart rate and the amplitude and dc component of the pulse wave at the peripheral blood vessel are measured, and the measured values are stored in the registers $RHR_2$, $RAC_2$, and $RDC_2$ of the RAM 18.

Then, in Step S7, it is judged whether or not the data of the pulse wave propagation time $T_1$ is present. If the data is present, the pulse wave propagation time change $\Delta T$, the heart rate change $\Delta HR$, the pulse wave amplitude change rate $r_1$, and the pulse wave dc component change rate $r_2$ are calculated in Step 58. That is, the pulse wave propagation time change $\Delta T$ is calculated by the following equation.

$$\Delta T = |T_2 - T_1|$$

Further, the heart rate change $\Delta HR$, the pulse wave amplitude change rate $r_1$, and the pulse wave dc component change rate $r_2$ are calculated by the following equations.

$$\Delta HR = |HR_2 - HR_1|$$

$$r_1 = |(AC_2 - AC_1)/AC_1|$$

$$r_2 = |(DC_2 - DC_1)/DC_1|$$

After the pulse wave propagation time change $\Delta T$, the heart rate change $\Delta HR$, the pulse wave amplitude change rate $r_1$, and the pulse wave dc component change rate $r_2$ have been calculated, Step S9 will be executed. That is, in Step S9, it is judged whether or not the pulse wave propagation time change $\Delta T$ calculated in Step S8 exceeds the preset pulse wave propagation time change threshold ΔTs; it is judged whether or not the heart rate change ΔHR calculated in Step S8 exceeds the value ΔHRS equivalent to the preset heart rate change; it is judged whether or not the pulse wave amplitude change rate $r_1$ calculated in Step S8 exceeds the value $r_1s$ equivalent to the preset rate of change of the amplitude of the pulse wave at the peripheral blood vessel; and it is judged whether or not the pulse wave dc component change rate $r_2$ calculated in Step S8 exceeds the value $r_2s$ equivalent to the preset rate of change of the dc component of the pulse wave at the peripheral blood vessel. That is, it is judged whether or not $\Delta T > \Delta Ts$, $\Delta HR > \Delta HRs$, $r_1 > r_1s$, and $r_2 > r_2s$ are satisfied. If none of the above inequalities is satisfied, then, a series of operation is repeated starting at Step S2.

On the other hand, if any one of the inequalities $\Delta T > \Delta Ts$, $\Delta HR > \Delta HRs$, $r_2 > r_1s$, and $r_2 > r_2s$ is satisfied, it is assumed that a sudden turn for the worse such as a shock has occurred in the blood pressure fluctuation of the subject, Step S3 will be executed. In Step S3, in order to take care of the sudden turn for the worse in the blood pressure fluctuation of the subject, a blood pressure measurement is made using the cuff 2, and the measured value BP is written to a data area in the RAM 18. Then, in Step S4, the pulse wave propagation time $T_2$ stored in the register $RT_2$ is moved to the register $RT_1$; the heart rate $HR_2$ stored in the register $RHR_2$ is moved to the register $RHR_1$; the amplitude $AC_2$ of the pulse wave stored in the register $RAC_2$ is moved to the register $RAC_1$; and the dc component $DC_2$ of the pulse wave stored in the register $RDC_2$ is moved to the register $RDC_1$. Then, in Step S5, the blood pressure value BP measured in Step S3 is displayed on the display 16. Step S2 will thereafter be executed.

As described in the foregoing, this embodiment is characterized as constantly measuring the pulse wave propagation time and not only judging whether or not the pulse wave propagation time change ΔT exceeds the pulse wave propagation time change threshold ΔTs but also judging whether or not the cardiovascular dynamic changes ΔHR, $r_1$, $r_2$ exceed the thresholds thereof ΔHRs, $r_1s$, $r_2s$, so that a sudden turn for the worse in the blood pressure fluctuation of a subject can be monitored and a blood pressure measurement using the cuff 2 is made reliably if any one of the values exceeds the threshold thereof. Therefore, the burden given to the subject in the past can be reduced. In addition, this embodiment is also characterized as allowing a feeble blood pressure fluctuation that cannot be detected by the pulse wave propagation time change to be detected by the cardiovascular dynamic change. Therefore, a sudden turn for the worse in the blood pressure fluctuation of the subject can be monitored more reliably.

It should be noted that pulse wave propagation time counting processing may be made every heart beat or may be made in such a manner that the processing is executed at a predetermined time interval or for predetermined heart rates and an average of the counts can then be calculated. This technique of calculating the average allows accurate pulse wave propagation time counting free from irregularly occurring noise to be made.

As described in the foregoing, the blood pressure monitoring apparatuses as recited in claims 1 to 5 are characterized as not only judging whether or not the pulse wave propagation time change exceeds the preset pulse wave propagation time change threshold, but also judging whether or not the cardiovascular dynamic change, i.e., the heart rate change, the rate of change of the amplitude of the pulse wave at the peripheral blood vessel, or the rate of change of the dc component of the pulse wave at the peripheral blood vessel, exceed the preset cardiovascular dynamic change thresholds thereof and starting a blood pressure measurement for the subject if any one of the changes is judged to exceed the threshold thereof. Therefore, the burden given to the subject in the past can be reduced. In addition, the blood pressure monitoring apparatuses as recited in claims 1 to 5 are also characterized as allowing a feeble blood pressure fluctuation that cannot be detected by the pulse wave propagation time change to be detected by the cardiovascular dynamic change. Therefore, a sudden turn for the worse in the blood pressure fluctuation of the subject can be monitored more reliably.

What is claimed is:

1. A blood pressure monitoring apparatus comprising:

blood pressure measuring means for measuring blood pressure using a cuff;

storage means for storing a pulse wave propagation time change threshold and a cardiovascular dynamic change threshold, both thresholds being inputted from an external device;

time interval detection reference point detecting means for detecting a time interval detection reference point on a pulse wave at an aorta of a body;

pulse wave detecting means for detecting a pulse wave at a peripheral blood vessel appearing with a time delay with respect to said pulse wave at said aorta;

pulse wave propagation time counting means for counting a pulse wave propagation time based on detected outputs from said time interval detection reference point detecting means and said pulse wave detecting means;

pulse wave propagation time change calculating means for calculating a pulse wave propagation time change from said two pulse wave propagation times counted by said pulse wave propagation time counting means;

cardiovascular dynamic change calculating means for calculating a cardiovascular dynamic change from said time interval detection reference point or said pulse wave at said peripheral blood vessel;

first judging means for judging whether or not said pulse wave propagation time change calculated by said pulse wave propagation time change calculating means exceeds said pulse wave propagation time change threshold stored in said storage means;

second judging means for judging whether or not said cardiovascular dynamic change calculated by said cardiovascular dynamic change calculating means exceeds said cardiovascular dynamic change threshold stored in said storage means; and control means for controlling said blood pressure measuring means and for measuring blood pressure of a subject using said cuff if it is judged that said pulse wave propagation time change exceeds said pulse wave propagation time change threshold or if it is judged that said cardiovascular dynamic change exceeds said cardiovascular dynamic change threshold.

2. A blood pressure monitoring apparatus according to claim 1, wherein said storage means stores a cardiovascular dynamic change threshold equivalent to a heart rate change, said cardiovascular dynamic change calculating means calculates a heart rate change based on said time interval detection reference point detected by said time interval detection reference point detecting means, and said second judging means judges whether or not said heart rate change calculated by said cardiovascular dynamic change calculating means exceeds said cardiovascular dynamic change threshold equivalent to said heart rate change stored in said storage means.

3. A blood pressure monitoring apparatus according to claim 1, wherein said storage means stores a cardiovascular dynamic change threshold equivalent to a rate of change of an amplitude of a pulse wave at a peripheral blood vessel; said cardiovascular dynamic change calculating means calculates said rate of change of said amplitude of said pulse wave, which is a chronological rate of change of said amplitude of said pulse wave based on said pulse wave at said peripheral blood vessel detected by said pulse wave detecting means; and said second judging means judges whether or not said rate of change of said amplitude of said pulse wave calculated by said cardiovascular dynamic change calculating means exceeds said cardiovascular dynamic change threshold equivalent to said rate of change of said amplitude of said pulse wave of said peripheral blood vessel stored in said storage means.

4. A blood pressure monitoring apparatus according to claim 1, wherein said storage means stores a cardiovascular dynamic change threshold equivalent to a rate of change of a dc component of a pulse wave of a peripheral blood vessel; said cardiovascular dynamic change calculating means calculates said rate of change of said dc component of said pulse wave, which is a chronological rate of change of said dc component of said pulse wave based on said pulse wave at said peripheral blood vessel detected by said pulse wave detecting means; and said second judging means judges whether or not said rate of change of said dc component of said pulse wave calculated by said cardiovascular dynamic change calculating means exceeds said cardiovascular dynamic change threshold equivalent to said rate of change of said dc component of said pulse wave of said peripheral blood vessel stored in said storage means.

5. A blood pressure monitoring apparatus according to claim 1, wherein said storage means stores cardiovascular dynamic change thresholds respectively equivalent to a heart rate change, a rate of change of an amplitude of a pulse wave of a peripheral blood vessel, and a rate of change of a dc component of a pulse wave of a peripheral blood vessel; said cardiovascular dynamic change calculating means calculates not only said heart rate change based on said time interval detection reference point detected by said time interval detection reference point detecting means, but also said rate of change of said amplitude of said pulse wave, which is a chronological rate of change of said amplitude of said pulse wave and said rate of change of said dc component of said pulse wave, which is a chronological rate of change of said dc component of said pulse wave, based on said pulse wave at said peripheral blood vessel detected by said pulse wave detecting means; said second judging means judges whether or not said heart rate change calculated by said cardiovascular dynamic change calculating means exceeds said cardiovascular dynamic change threshold equivalent to said heart rate change stored in said storage means, whether or not said rate of change of said amplitude of said pulse wave calculated by said cardiovascular dynamic change calculating means exceeds said cardiovascular dynamic change threshold equivalent to said rate of change of said amplitude of said pulse wave of said peripheral blood vessel stored in said storage means, and whether or not said rate of change of said dc component of said pulse wave calculated by said cardiovascular dynamic change calculating means exceeds said cardiovascular dynamic change threshold equivalent to said rate of change of said dc component of said peripheral blood vessel stored in said storage means; and said control means controls said blood pressure measuring means and measures blood pressure of a subject using said cuff if it is judged that said heart rate change exceeds said cardiovascular dynamic change threshold equivalent to said heart rate change, if it is judged that said rate of change of said amplitude of said pulse wave exceeds said cardiovascular dynamic change threshold equivalent to said rate of change of said amplitude of said pulse wave of said peripheral blood vessel, or if it is judged that said rate of change of said dc component of said pulse wave exceeds said cardiovascular dynamic change threshold equivalent to said rate of change of said dc component of said pulse wave of said peripheral blood vessel.

6. A blood pressure monitoring method comprising said steps of:

measuring blood pressure using cuff;

storing a pulse wave propagation time change threshold and a cardiovascular dynamic change threshold, both thresholds being inputted from an external device;

detecting a time interval detection reference point on a pulse wave at an aorta of a body;

detecting a pulse wave at a peripheral blood vessel appearing with a time delay with respect to said pulse wave at said aorta;

counting a pulse wave propagation time based on detected outputs from said time interval detection reference point and said pulse wave;

calculating a pulse wave propagation time change from said two pulse wave propagation times counted;

calculating a cardiovascular dynamic change from said time interval detection reference point or said pulse wave at said peripheral blood vessel;

judging whether or not said pulse wave propagation time change calculated exceeds said pulse wave propagation time change threshold stored;

judging whether or not said cardiovascular dynamic change exceeds said cardiovascular dynamic change threshold; and measuring blood pressure of a subject using said cuff if it is judged that said pulse wave propagation time change exceeds said pulse wave propagation time change threshold or if it is judged that said cardiovascular dynamic change exceeds said cardiovascular dynamic change threshold.

7. A blood pressure monitoring apparatus comprising:

blood pressure measuring means for measuring blood pressure using a cuff;

storage means for storing a pulse wave propagation time change threshold and a cardiovascular dynamic change threshold, both thresholds being inputted from an external device;

time interval detection reference point detecting means for detecting a time interval detection reference point on a pulse wave at an aorta of a body;

pulse wave detecting means for detecting a pulse wave at a peripheral blood vessel appearing with a time delay with respect to said pulse wave at said aorta;

pulse wave propagation time counting means for counting a pulse wave propagation time based on detected outputs from said time interval detection reference point detecting means and said pulse wave detecting means;

pulse wave propagation time change calculating means for calculating a pulse wave propagation time change from said two pulse wave propagation times counted by said pulse wave propagation time counting means;

main judgement means for judging whether or not a condition of an subject is changed on the basis of a result of said pulse wave propagation time change calculating means;

cardiovascular dynamic change calculating means for calculating a cardiovascular dynamic change from said time interval detection reference point or said pulse wave at said peripheral blood vessel;

auxiliary judging means for judging whether or not said cardiovascular dynamic change calculated by said cardiovascular dynamic change calculating means exceeds said cardiovascular dynamic change threshold stored in said storage means, main control means for controlling said blood pressure measuring means and for measuring blood pressure of a subject using said cuff in accordance with a result of said main judging means and auxiliary judging means;

wherein said main judging means for judging whether or not said pulse wave propagation time change calculated by said pulse wave propagation time change calculating means exceeds said pulse wave propagation time change threshold stored in said storage means, and said main control means for controlling said blood pressure measuring means and for measuring blood pressure of a subject using said cuff if it is judged that said pulse wave propagation time change exceeds said pulse wave propagation time change threshold or if it is judged that said cardiovascular dynamic change exceeds said cardiovascular dynamic change threshold.

8. A blood pressure monitoring apparatus according to claim 7, wherein said storage means stores a cardiovascular dynamic change threshold equivalent to a heart rate change, said cardiovascular dynamic change calculating means calculates a heart rate change based on said time interval detection reference point detected by said time interval detection reference point detecting means, and said second judging means judges whether or not said heart rate change calculated by said cardiovascular dynamic change calculating means exceeds said cardiovascular dynamic change threshold equivalent to said heart rate change stored in said storage means.

9. A blood pressure monitoring apparatus according to claim 7, wherein said storage means stores a cardiovascular dynamic change threshold equivalent to a rate of change of an amplitude of a pulse wave at a peripheral blood vessel; said cardiovascular dynamic change calculating means calculates said rate of change of said amplitude of said pulse wave, which is a chronological rate of change of said amplitude of said pulse wave based on said pulse wave at said peripheral blood vessel detected by said pulse wave detecting means; and said second judging means judges whether or not said rate of change of said amplitude of said pulse wave calculated by said cardiovascular dynamic change calculating means exceeds said cardiovascular dynamic change threshold equivalent to said rate of change of said amplitude of said pulse wave of said peripheral blood vessel stored in said storage means.

10. A blood pressure monitoring apparatus according to claim 7, wherein said storage means stores a cardiovascular dynamic change threshold equivalent to a rate of change of a dc component of a pulse wave of a peripheral blood vessel; said cardiovascular dynamic change calculating means calculates said rate of change of said dc component of said pulse wave, which is a chronological rate of change of said dc component of said pulse wave based on said pulse wave at said peripheral blood vessel detected by said pulse wave detecting means; and said second judging means judges whether or not said rate of change of said dc component of said pulse wave calculated by said cardiovascular dynamic change calculating means exceeds said cardiovascular dynamic change threshold equivalent to said rate of change of said dc component of said pulse wave of said peripheral blood vessel stored in said storage means.

11. A blood pressure monitoring apparatus according to claim 7, wherein said storage means stores cardiovascular dynamic change thresholds respectively equivalent to a heart rate change, a rate of change of an amplitude of a pulse wave of a peripheral blood vessel, and a rate of change of a dc component of a pulse wave of a peripheral blood vessel; said cardiovascular dynamic change calculating means calculates not only said heart rate change based on said time interval detection reference point detected by said time interval detection reference point detecting means, but also said rate of change of said amplitude of said pulse wave, which is a chronological rate of change of said amplitude of said pulse wave and said rate of change of said dc component of said pulse wave, which is a chronological rate of change of said dc component of said pulse wave, based on said pulse wave at said peripheral blood vessel detected by said pulse wave detecting means; said second judging means judges whether or not said heart rate change calculated by said cardiovascular dynamic change calculating means exceeds said cardiovascular dynamic change threshold equivalent to said heart rate change stored in said storage means, whether or not said rate of change of said amplitude of said pulse wave calculated by said cardiovascular dynamic change calculating means exceeds said cardiovascular dynamic change threshold equivalent to said rate of change of said amplitude of said pulse wave of said peripheral blood vessel stored in said storage means, and whether or not said rate of change of said dc component of said pulse wave calculated by said cardiovascular dynamic change calculating means exceeds said cardiovascular dynamic change threshold equivalent to said rate of change of said dc component of said peripheral blood vessel stored in said storage means; and said control means controls said blood pressure measuring means and measures blood pressure of a subject using said cuff if it is judged that said heart rate change exceeds said cardiovascular dynamic change threshold equivalent to said heart rate change, if it is judged that said rate of change of said amplitude of said pulse wave exceeds said cardiovascular dynamic change threshold equivalent to said rate of change of said amplitude of said pulse wave of said peripheral blood vessel, or if it is judged that said rate of change of said dc component of said pulse wave exceeds said cardiovascular dynamic change threshold equivalent to said rate of change of said dc component of said pulse wave of said peripheral blood vessel.

12. A blood pressure monitoring method comprising said steps of:

storing a pulse wave propagation time change threshold and a cardiovascular dynamic change threshold, both thresholds being inputted from an external means;

detecting a time interval detection reference point on a pulse wave at an aorta of a body;

detecting a pulse wave at a peripheral blood vessel appearing with a time delay with respect to said pulse wave at said aorta;

counting a pulse wave propagation time based on detected outputs from said time interval detection reference point and said pulse wave;

calculating a pulse wave propagation time change from said two pulse wave propagation times counted;

calculating a cardiovascular dynamic change from said time interval detection reference point or said pulse wave at said peripheral blood pressure;

judging whether or not said pulse wave propagation time change calculated exceeds said pulse wave propagation time change threshold stored;

judging whether or not said cardiovascular dynamic change exceeds said cardiovascular dynamic change threshold; and measuring blood pressure of a subject using said cuff if it is judges that said pulse wave propagation time change exceeds said pulse wave propagation time change threshold or if it is judged that said cardiovascular dynamic change exceeds said cardiovascular dynamic change threshold.

13. A blood pressure monitoring apparatus comprising:

blood pressure measuring means for measuring blood pressure using a cuff;

time interval detection reference point detecting means for detecting a time interval detection reference point for counting pulse wave propagation time;

pulse wave detection means for detecting a pulse wave at a peripheral blood vessel appearing with a time delay with respect to said pulse wave at an aorta;

pulse wave propagation time counting means for counting a pulse wave propagation time based on detected outputs from said time interval detection reference point detecting means and said pulse wave detecting means;

cardiovascular dynamic change calculating means for calculating a cardiovascular dynamic change from said time interval detection reference point or said pulse wave at said peripheral blood vessel;

control means for controlling said blood pressure measurement means on the basis of the change of pulse wave propagation time, counted by said pulse wave propagation time counting means and the cardiovascular dynamic change calculated by said cardiovascular dynamic change calculating means so that the blood pressure of a subject is measured using the cuff.

14. The blood pressure monitoring apparatus according to claim 13, wherein said cardiovascular dynamic change is equivalent to at least one of a heart rate change, change of amplitude of the pulse wave of said peripheral blood vessel, and change of dc component of the pulse wave of said peripheral blood vessel.

15. The blood pressure measuring apparatus according to claim 13, wherein said time interval detection reference point detection means includes an electrode to be attached to a subject, and determines an electrocardiographic R wave as the time interval detection reference point.

16. A blood pressure monitoring apparatus comprising:

blood pressure measuring means for measuring blood pressure using a cuff;

time interval detection reference point detecting means for detecting a time interval detection reference point for counting pulse wave propagation time;

pulse wave detection means for detecting a pulse wave at a peripheral blood vessel appearing with a time delay with respect to said pulse wave at an aorta;

pulse wave propagation time counting means for counting a pulse wave propagation time based on detected outputs from said time interval detection reference point detecting means and said pulse wave detecting means;

cardiovascular dynamic change calculating means for calculating a cardiovascular dynamic change from said time interval detection reference point or said pulse wave at said peripheral blood vessel;

first judging means for judging whether or not change of pulse wave propagation time counted by said pulse wave propagation time counting means exceeds a first predetermined threshold;

second judging means for judging whether or not said cardiovascular dynamic change calculated by said cardiovascular dynamic change calculating means exceeds a second predetermined threshold; and control means for controlling said blood pressure measuring means and for measuring blood pressure of a subject using said cuff under at least one of condition that said first judging means judges that the change of pulse wave propagation time counted by said pulse wave propagation time counting means exceeds the first predetermined threshold and the condition that said second judging means judges that said cardiovascular dynamic change calculated by said cardiovascular dynamic change calculating means exceeds the second predetermined threshold.

17. The blood pressure monitoring apparatus according to claim 16, wherein said cardiovascular dynamic change is equivalent to at least one of a heart rate change, change of amplitude of the pulse wave of said peripheral blood vessel, and change of dc component of the pulse wave of said peripheral blood vessel.

18. The blood pressure monitoring apparatus according to claim 16, wherein said cardiovascular dynamic change calculating means calculates heart rate changes based on said time interval detection reference point by said time interval detection reference point detecting means; and wherein said second judging means judges whether or not said heart rate change calculated by said cardiovascular dynamic change calculating means exceeds said second predetermined threshold which is equivalent to heart rate change.

19. The blood pressure monitoring apparatus according to claim 16, wherein said cardiovascular dynamic change calculating means calculates a change of amplitude of said pulse wave at said peripheral blood vessel detected by said pulse wave detecting means; and wherein said second judging means judges whether or not said changes of amplitude of said pulse wave calculated by said cardiovascular dynamic change calculating means exceeds said second predetermined threshold which is equivalent to changes of amplitude of the pulse wave of said peripheral blood vessel.

20. The blood pressure monitoring apparatus according to claim 16, wherein said cardiovascular dynamic change calculating means calculates a change of dc component of said pulse wave at said peripheral blood vessel detected by said pulse wave detecting means; and wherein said second judging means judges whether or not said changes of dc component of said pulse wave calculated by said cardiovascular dynamic change calculating means exceeds said second predetermined threshold which is equivalent to changes of dc component of the pulse wave of said peripheral blood vessel.

21. The blood pressure measuring apparatus according to claim 16, wherein said time interval detection reference point detection means includes an electrode to be attached to a subject and determines an electrocardiographic R wave as the time interval detection reference point.

22. A blood pressure monitoring apparatus comprising:

blood pressure measuring means for measuring blood pressure using a cuff;

time interval detection reference point detecting means for detecting a time interval detection reference point for counting a pulse wave propagation time;

pulse wave detection means for detecting a pulse wave at a peripheral blood vessel appearing with a time delay with respect to said pulse wave at an aorta;

pulse wave propagation time counting means for counting a pulse wave propagation time based on detected outputs from said time interval detection reference point detecting means and said pulse wave detecting means;

main judgement means for judging whether or not a condition of a subject is changed on the basis of change of pulse wave propagation time counted by said pulse wave propagation time counting means;

cardiovascular dynamic change calculating means for calculating a cardiovascular dynamic change from said time interval detection reference point or said pulse wave at said peripheral blood vessel;

auxiliary judging means for judging whether or not said cardiovascular dynamic change calculated by said cardiovascular dynamic change calculating means exceeds a second predetermined threshold;

main control means for controlling said blood pressure measuring means and for measuring blood pressure of a subject using said cuff in accordance with a result of said main judging means and auxiliary judging means;

wherein said main judging means judges whether or not the change of pulse wave propagation time calculated by said pulse wave propagation time counting means exceeds a first predetermined threshold, and wherein said main control means controls said blood pressure measuring and measures blood pressure of a subject using said cuff under at least one condition selected from the condition that it is judged that said change of amount relating to pulse wave propagation time exceeds the first predetermined threshold and the condition that it is judged that said cardiovascular dynamic change exceeds the second predetermined threshold.

23. The blood pressure monitoring apparatus according to claim 22, wherein said cardiovascular dynamic change is equivalent to at least one of a heart rate change, change of amplitude of the pulse wave of said peripheral blood vessel, and change of dc component of the pulse wave of said peripheral blood vessel.

24. The blood pressure monitoring apparatus according to claim 22, wherein said cardiovascular dynamic change calculating means calculates heart rate changes based on said time interval detection reference point detected by said time interval detection reference point detecting means, and wherein said auxiliary judging means judges whether or not said heart rate change calculated by said cardiovascular dynamic change calculating means exceeds said second predetermined threshold which is equivalent to heart rate change.

25. The blood pressure monitoring apparatus according to claim 22, wherein said cardiovascular dynamic change calculating means calculates a change of amplitude of said pulse wave at said peripheral blood vessel detected by said pulse wave detecting means; and wherein said auxiliary judging means judges whether or not said changes of amplitude of said pulse wave calculated by said cardiovascular dynamic change calculating means exceeds second predetermined threshold which is equivalent to changes of amplitude of the pulse wave of said peripheral blood vessel.

26. The blood pressure monitoring apparatus according to claim 22, wherein said cardiovascular dynamic change calculating means calculates a change of dc component of said pulse wave at said peripheral blood vessel detected by said pulse wave detecting means; and wherein said auxiliary judging means judges whether or not said changes of dc component of said pulse wave calculated by said cardiovascular dynamic change calculating means exceeds said second predetermined threshold which is equivalent to changes of dc component of the pulse wave of said peripheral blood vessel.

27. The blood pressure measuring apparatus according to claim 22, wherein said time interval detection reference point detection means includes an electrode to be attached to a subject, and determines an electrocardiographic R wave as the time interval detection reference point.

28. A blood pressure monitoring apparatus comprising:

blood pressure measuring means for measuring blood pressure using a cuff;

pulse wave propagation time measurement means for measuring pulse wave propagation time;

cardiovascular dynamic change calculating means for calculating a cardiovascular dynamic change;

control means for controlling said blood pressure measuring means on the basis of a change of pulse wave propagation time measured by said pulse wave propagation time measurement means and the cardiovascular dynamic change calculated by said cardiovascular dynamic change calculating means, so that the blood pressure of a subject is measured using the cuff.

29. The blood pressure monitoring apparatus according to claim 28, wherein said cardiovascular dynamic change is equivalent to at least one of a heart rate change, change of amplitude of a pulse wave, and change of dc component of a pulse wave.

30. The blood pressure measuring apparatus according to claim 28, wherein said pulse wave propagation time measurement means includes time interval detection reference point detection means having an electrode to be attached to a subject, and determines an electrocardiographic R wave as a time interval reference point.

* * * * *